United States Patent [19]

Turk

[11] Patent Number: 5,229,161
[45] Date of Patent: Jul. 20, 1993

[54] METAL FREE AND LOW METAL SALT SUBSTITUTES CONTAINING LYSINE

[75] Inventor: Richard Turk, East Lansing, Mich.

[73] Assignee: Michigan Biotechnology Institute, Lansing, Mich.

[21] Appl. No.: 925,722

[22] Filed: Aug. 4, 1992

[51] Int. Cl.$^5$ ................. A23L 1/227; A23L 1/237
[52] U.S. Cl. ................... 426/649; 426/650; 426/656
[58] Field of Search ............... 426/649, 650, 656

[56] References Cited

U.S. PATENT DOCUMENTS

| | | | |
|---|---|---|---|
| 1,874,055 | 8/1932 | Liebrecht | 426/649 |
| 2,824,008 | 2/1958 | Perri | 426/649 |
| 2,829,056 | 4/1958 | Kemmerer | 426/649 |
| 3,015,567 | 1/1962 | Hause | 426/650 |
| 3,993,795 | 11/1976 | Mauron et al. | 426/618 |
| 4,064,138 | 12/1977 | Saari et al. | 548/344 |
| 5,145,707 | 9/1992 | Lee | 426/649 |
| 5,173,323 | 12/1992 | Omari | 426/649 |
| 5,176,934 | 1/1993 | Lee | 426/649 |

*Primary Examiner*—Jeanette Hunter
*Assistant Examiner*—Mary S. Mims
*Attorney, Agent, or Firm*—Quarles & Brady

[57] ABSTRACT

Salts containing lysine, chloride ion and succinic acid in which the lysine is present in greater molar concentration than the chloride or succinic acid possess a salty flavor making them useful as table salt substitutes and flavor enhancers. Low sodium and low potassium salts containing sodium or potassium in addition to the lysine, chloride ion and succinic acid also are disclosed.

21 Claims, No Drawings

METAL FREE AND LOW METAL SALT SUBSTITUTES CONTAINING LYSINE

This invention was made with government support under Federal Grant 90-34189-5014 awarded by the U.S. Department of Agriculture. The government has certain rights in the invention.

FIELD OF THE INVENTION

The present invention relates to salt substitutes. More particularly, it relates to novel amino acid derivatives that have a salty taste and flavor and which can be substituted for table salt (NaCl).

BACKGROUND OF THE INVENTION

Present salt substitutes attempt to simulate the taste and appearance of sodium chloride. Nu-Salt ® (Cumberland Packing Corp. U.S.A.) contains potassium chloride. No-Salt ® (RCN Products U.S.A.) also contains potassium chloride. Lite Salt ® (Morton International) is a 50:50 blend of sodium and potassium chlorides. Still another product Papa Dash TM (Alberto Culver U.S.A.) contains malto-dextrin, NaCl and potassium iodide. The potassium containing products have limited application due to their bitter and metallic taste.

Although they are not salt substitutes, flavor enhancers, such as monosodium glutamate and sodium inosinate, often are added to various food formulations to enhance the saltiness of salted food. However, these materials do not have a salty taste.

Various attempts have been made to develop organic products which have a salty taste like sodium chloride and the ability to enhance flavors.

In the Hause et al. U.S. Pat. No. 3,015,567 the compounds L-lysine succinate, L-lysine hydrogen succinate and L-lysine hydrogen adipate are described as having "the unique property of having a desirable salty taste which improves the flavor of food to which they are added." However, the high acidity and sourness due to the combination of organic acids and mineral acids make these compounds unacceptable for use as table salt replacements. As a result, although the patent has now expired, those compounds still have not found any acceptance as salt substitutes.

A need still exists for a salt substitute that does not have the disadvantages of table salt or prior art table salt substitutes.

BRIEF SUMMARY OF THE INVENTION

It is an object of the present invention to disclose compounds having a salty taste and the ability to enhance flavors.

It also is an object to disclose sodium-free and potassium-free salts and low sodium and low potassium salts and blends thereof, that have both an intense salty taste and a pleasant flavor.

It has been discovered that unique sodium-free and potassium-free salts containing various molar ratios of L-lysine, succinic acid and chloride ion possess a desirable salty taste. This discovery was unexpected because L-lysine, a sweet tasting amino acid, and succinic acid, a sour tasting acid, when combined in molar ratios of 1:1 or 2:1 as proposed in the Hause et al patent result in salts having a sour and less intense salty taste.

The sodium-free and potassium-free salts which contain only L-lysine, chloride ion and succinic acid have a saltiness which resembles that of sodium chloride without having the sodium which has been linked to hypertension in man.

The preferred sodium-free and potassium-free salts of the present invention are those containing L-lysine, chloride ion and succinic acid in the molar ratios of 2:1:1 or 4:3:2 or 8:3:4 or 8:5:4 or 16:7:8 or 32:5:16. All of these salts contain more lysine molecules than either chloride ions or succinic acid molecules.

The preferred low sodium and low potassium salts of the present invention are the salts which in addition to sodium or potassium ions also contain L-lysine, chloride ion and succinic acid in the molar ratios of 2:1:1 or 4:3:2 or 8:3:4 or 8:5:4 or 16:7:8 or 32:5:16. These compounds contain much lower concentrations of sodium (monosodium 4.3% and disodium 8.6% by weight) than sodium chloride (39+%) or monosodium glutamate MSG (12+%). A preferred compound contains lysine, chloride ion, succinic acid and sodium in molar ratio of 8:5:4:1; it contains only 1.22% sodium by weight and it has a very salty taste. The low potassium salts have similar low concentrations of potassium. In addition to the monosodium and monopotassium salts, salts can be prepared containing two, three or more ions of sodium or potassium. If desired, salts also can be prepared which are iodized, i.e., one or more HCl's are replaced by HI.

The salts of the present invention may be represented by the following formula unit:

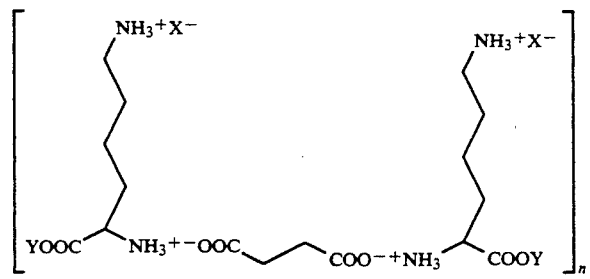

in which n is 1 to 16 formula units; Y is H, Na or K and can be the same or different; and X is OH or halogen, such as chlorine (Cl) or iodine (I) or fluorine (F) and at least one but not all X's are Cl.

This convention for ionic compounds indicates that the compound can be made in a manner consistent with the molar ratio of its component ingredients. The number of formula units is typically between 1 and 16 and represents the addition of 2 to 32 molecules of lysine. Each of the formula units consists of lysine and succinic acid in the molar ratio of 2 to 1. The remaining cations, Y, and anions, X, are required for maintaining an appropriate pH during drying and maintaining charge neutrality. The symbol Y represents cations H, Na and K. A salt that is alkali metal free can be prepared from succinic acid and lysine. In this case, all Y's are represented by hydrogen, H. If a sodium free formulation is desired, an amount of potassium ions can be added to substitute for some of the protons. A salt can be prepared with a minimum of 1 potassium per 32 lysine molecules when n is 16. This salt will contain 0.27% potassium by weight based on the formula mass. A salt can be prepared with a maximum of 32 potassium atoms per 32 lysine molecules when n is 16. This salt will contain 8.8% potassium by weight based on the formula mass. A sodium containing salt can also be prepared by substituting sodium ions for protons. A salt can be prepared with a minimum of 1 sodium ion per 32 lysines. This salt will contain 0.28% sodium weight based on the formula mass. A salt can be prepared with a maximum of 32 sodium ions per 32 lysine molecules. This salt will contain 9.1% sodium by weight based on the formula mass.

The anions $X^-$, will normally represent hydroxide ions, OH. It has been found that the salts of the invention will range in organoleptic properties from sweet to salty to sour. The organoleptic properties can be adjusted by substituting one of the halide ions $Cl^-$, $I^-$ or $F^-$ for a hydroxide ion. A minimum of one halide ion can be added to the formula per 32 lysine molecules when n is 16. A maximum of 31 chloride ions can be added per 32 lysine molecules. The addition of 32 chloride ions results in the substitution of all hydroxide ions and gives an undesirable sour taste.

It has also been determined that during the drying of the salts, various states of hydration may occur. The ingredients lysine monohydrochloride, lysine monohydrate, and sodium succinate, all exist as hydrates. It has been found that the number of waters of hydration present depends on the number of chlorine atoms, sodium ions and succinic acid molecules in the formula unit. There may be 1 to 3 water molecules of hydration per formula unit.

The salts of the present invention can be readily prepared by common salt forming procedures or by methods which use conventional electrodialysis to reduce the chloride content of L-lysine monohydrochloride when it is used as a source of lysine.

The salts of the present invention, in addition to being salt substitutes, may be useful as preservatives because of the properties of succinic acid.

The foregoing and other advantages of the salts of the present invention will become apparent to those skilled in the art from the description of the preferred embodiments.

DESCRIPTION OF THE PREFERRED EMBODIMENTS

The preferred sodium-free and potassium-free salts are those containing L-lysine, chloride ion and succinic acid in the molar ratios of 2:1:1, 4:3:2, 8:3:4, 8:5:4, 16:7:8 and 32:5:16. They may conveniently be prepared by dissolving L-lysine monohydrochloride and L-lysine monohydrate in water and adding succinic acid to the solution. The solution is dried in an oven until solids begin to form when the solution is cooled to room temperature. If desired, the solids can be ground to obtain a free-flowing powder.

The preferred low sodium or low potassium salts are those containing L-lysine, chloride ion, succinic acid and sodium or potassium in the molar ratios of 2:1:1:1, 4:3:2:1, 8:5:4:1, 8:3:4:1, 16:7:8:1 and 32:5:16:1. They may be prepared by dissolving L-lysine monohydrate in water, adding hydrochloric acid, disodium succinate or dipotassium succinic and succinic acid. If necessary sodium hydroxide or potassium hydroxide can be used to adjust to the desired molar ratio.

The following examples illustrate the preparation of the salts of the present invention:

EXAMPLE 1

Preparation of 2:1:1 Salt 10 grams of L-lysine monohydrochloride and 8.95 grams of L-lysine monohydrate are dissolved in 25 ml of water. 6.5 grams of succinic acid is added and dissolved. The solution is then dried in a 110° C. oven until solids begin to form when cooled to room temperature. After 15 to 30 minutes solids form at room temperature and are collected.

EXAMPLE 2

Preparation of 2:1:1 Salt

The procedure of Example 1 is repeated using as the source of L-lysine and chloride ions 17.9 gms of L-lysine monohydrate and 8.95 ml of concentrated hydrochloric acid.

EXAMPLE 3

Preparation of 2:1:1 Salt

A 20% solution of L-lysine monohydrochloride is subjected to conventional electrodialysis so that chloride content is reduced from 19.4% by weight solids to 9.7% by weight solids. Succinic acid is added at a ratio of 1 mole succinic acid per 2 moles of L-lysine. [L-lysine can be determined by heating at 37° C., 0.2 ml of solution and 2.0 ml of 2% ninhydrin for 15 minutes. The red color can be measured spectrophotometrically at 500 nm and compared to an L-lysine standard.] The solution is dried and solids collected as in Example 1.

EXAMPLE 4

Preparation of 2:1:1:1 (Sodium) Salt 12 grams of L-lysine monohydrate is dissolved in 20 ml of water to which 6.0 ml of concentrated hydrochloric acid has been added. 2.964 grams of disodium succinate is added to neutralize some of the excess hydrochloric acid and 2.16 grams of succinic acid are added with mixing until effervescence ceases and all solids are dissolved. The solution is dried in a 110° C. oven until solids begin to form when cooled to room temperature. After 15 to 30 minutes solids form and are collected.

EXAMPLE 5

Preparation of 2:1:1:1 (Sodium) Salt

L-lysine monohydrochloride is subjected to conventional electrodialysis which reduces the chloride content from 19.4% by weight solids to 9.7% by weight solids. The sodium concentration is adjusted to 500 milliequivalents of sodium per 1 mole of L-lysine with sodium hydroxide or sodium chloride. Succinic acid is added at a ratio of i mole succinic acid per 2 moles of L-lysine. The resulting solution is dried and the solids collected as in Example 1.

The salts containing the ingredients in the other molar ratios can be prepared by the same procedures.

All of the ingredients used in preparing the salts are readily available.

Presently L-lysine is an essential amino acid which is commercially available. The lysine monohydrate and the lysine hydrochloride are available from various sources (such as Ajinomoto, Degussa, ADM and Bio Kyowa, Inc.)

Succinic acid is available from numerous sources. It can be synthesized from maleic anhydride or prepared by fermentation. It is approved as a food additive in relishes and condiments. It has a limited application as a food acidulant but is not as widely used as citric, lactic, malic, and fumaric acids. Succinic acid also has been used as an additive in various fermented foods such as soy, soy paste and sake. Salts also can be prepared using sodium succinate which acts as a buffer to reduce acidity.

In Table 1 the properties of the salts of the present invention and those of the prior art are compared. In Table 1 the notation (Ratio) is used to quantitate the molar ratio of the L-lysine, chloride ion, succinic acid and, if present, sodium or potassium ion. For example 4:3:2 indicates 1 mole of lysine monohydrate, $\mu$ mole of HCl, and ½ mole of succinic acid in the salt. Table 1 also shows the pH of an aqueous solution, and the taste profile for the various salts as determined by organoleptic evaluation in edible foods.

TABLE I

| Ratio | pH | Taste | Na+ or K+ Content % |
|---|---|---|---|
| 2:2:0 | 3.3 | sweet | 0 |
| 2:0:1 | 6.5 | no taste | 0 |
| 2:0:2 | 7.1 | sour | 0 |
| 2:2:1 | 3.3 | salty/sour | 0 |
| 2:1:1 | 4.9 | salty | 0 |
| 4:3:2 | 3.8 | salty | 0 |
| 4:1:2 | 5.3 | weakly salty | 0 |
| 8:3:4 | 4.8 | salty | 0 |
| 8:5:4 | 4.3 | salty | 0 |
| 2:1:1:1(Na) | 4.9 | salty | 4.5 |
| 4:3:2:1(Na) | 3.8 | salty | 2.1 |
| 8:3:4:1(Na) | 4.8 | salty | 1.2 |
| 8:5:4:1(Na) | 4.3 | salty | 1.1 |
| 2:1:1:1(K) | 4.8 | salty | 4.5 |
| 4:3:2:1(K) | 3.8 | salty | 2.1 |
| 8:3:4:4(K) | 4.8 | salty | 4.5 |
| 8:5:4:1(K) | 4.3 | salty | 1.1 |
| 16:7:8:8(Na) | 4.6 | salty | 4.5 |
| 32:5:16:1(Na) | 5.4 | salty | 0.3 |

The salts of the present invention show promise as also being flavor enhancers which do not contain high percentages of sodium. The flavor enhancer, monosodium glutamate contains 12.5% sodium by weight and the monosodium salt of lysine succinate Hcl (2:1:1:1) of the present invention which is a flavor enhancer contains only 4.5% sodium by weight.

An alternative method of preparing the salts employs lysine monohydrochloride which is the cheapest feedstock. However, the direct addition of succinic acid to this material results in a salt which is too acidic. Several options are available for removal of this acidity:

1. If the sodium-free salt is desired up to ½ mole of HCl must be removed per mole of lysine. This can be achieved by using electrodialysis in which the monohydrate free base and hydrochloric acid are made in the base and acid compartments, respectively. The use of electrodialysis provides the correct lysine Cl/lysine OH ratio and produces HCl. Conventional electrodialysis also can be used to produce the correct lysine Cl/lysine OH ratio. Alternatively anion exchange resins could be used to remove ½ equivalent of chloride from lysine monohydrochloride.

2. If the monosodium salt is desired the material can easily be formulated by addition of sodium succinate and succinic acid or with NaOH and succinic acid.

A substitute for Lite Salt ® (50:50 NaCl:KCl) which can contain up to 19.7% sodium may be prepared by adding 1.548 lbs. of NaCl per 1.548 lbs. of salt 8:3:4. The monosodium salt could be formulated up to 10% by weight in a reduced salt application (i.e. cheeses, snacks, meats, dressings, spices, peanut butter, butter topping).

In addition to serving as a direct substitute for table salt other potential applications of the salts of the present invention are as flavor enhancers, food additives and pharmaceutical ingredients. Further applications may, for example, be based on the solubility behavior of the salts and the functionality of the amino and carboxylic acid groups which can bind to fats, oils, proteins and flavor compounds. The salts might also be used in place of NaCl in cereals, soups, salad dressings, snacks, carbonated beverages, sauces, pickled products, nut products, baked goods, canned vegetables, gravies, meat, meat products, baby foods, cheeses, cottage cheese, and seasonings. They might also be added to improve the microwavability of prepared foods. If desired, iodine and minerals can be added to the salts, as well as anticaking agents.

It will be readily apparent to those skilled in the art that a number of modifications and changes can be made without departing from the spirit and scope of the invention. Therefore, it is intended that the invention only be limited by the claims.

I claim:

1. A salt of the formula:

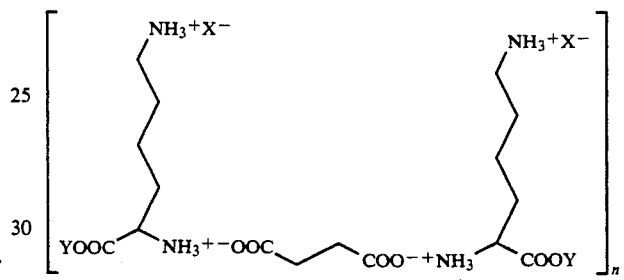

in which n is 1 to 16 formula units; Y is H, Na or K and can be the same or different, and X is OH or a halogen, such as Cl or I or F, wherein at least 1 but not all X's are Cl.

2. A salt of claim 1 in which Y is only H.

3. A low sodium salt of claim 1 in which Y is selected from H and Na, at least 1 Y is Na, and the weight percentage of sodium is between 0.25% and 9.1%.

4. A sodium free salt of claim 1 in which Y is H or K and the weight percentage of potassium is between 0.25% and 8.8%.

5. A salt of claim 1 in which n is 2, Y is H only, and two X's are OH and the other two X's are Cl.

6. A salt of claim 1 in which n is 4, Y is H only, and three X's are OH and five X's are Cl.

7. A salt of claim 1 in which n is 4, Y is H only, and five X's are OH and three X's are Cl.

8. A salt of claim 1 in which at least one Y of one formula unit is Na and the remaining are H.

9. A salt of claim 1 in which at least one Y of one formula unit is K and the remaining are H.

10. A salt of claim 1 in which there are one to three water molecules of hydration.

11. A salt of claim 1 in which at least one X of one formula unit is I.

12. A table salt substitute containing a salt of claim 1.

13. A food product containing a salt of claim 1.

14. A flavor enhancer containing a salt of claim 1.

15. A composition comprising lysine, chloride ion, and succinic acid, said composition containing more lysine molecules than chloride ions or succinic acid molecules.

16. A composition of claim 15 in which the lysine, chloride ion, and succinic acid are present in a molar ratio of about 2:1:1.

17. A composition of claim 15 in which the lysine, chloride ion, and succinic acid are present in a molar ratio of about 8:3:4.

18. A composition of claim 16 which also contains Na or K.

19. A composition of claim 17 which also contains Na or K.

20. A table salt substitute or flavor enhancer containing as an essential ingredient a composition of claim 15.

21. A composition of claim 15 in which the lysine is selected from L-lysine, D-lysine and DL-lysine.

* * * * *